United States Patent [19]

Kallenbach

[11] Patent Number: 5,364,976
[45] Date of Patent: Nov. 15, 1994

[54] ALKYLATION/ETHERIFICATION PROCESS

[75] Inventor: Lyle R. Kallenbach, Bartlesville, Okla.

[73] Assignee: Phillips Petroleum Company, Bartlesville, Okla.

[21] Appl. No.: 145,270

[22] Filed: Oct. 29, 1993

[51] Int. Cl.$^5$ .................. C07C 41/06; C07C 41/09; C10L 1/02
[52] U.S. Cl. .................. 568/697; 44/449; 568/698; 585/301
[58] Field of Search ............ 568/697, 698; 44/449; 585/301

[56] References Cited

U.S. PATENT DOCUMENTS

| | | | |
|---|---|---|---|
| 2,720,547 | 10/1955 | Wolff et al. | 260/614 |
| 3,887,635 | 6/1975 | Parker et al. | 260/683.47 |
| 3,984,352 | 10/1976 | Rodewald | 252/436 |
| 4,454,356 | 6/1984 | Masilamani et al. | 568/697 |
| 4,613,723 | 9/1986 | Olah | 585/730 |
| 4,709,101 | 11/1987 | Masilamani et al. | 568/697 |
| 4,783,567 | 11/1988 | Kocal | 585/464 |
| 5,220,095 | 6/1993 | Hommeltoft et al. | 585/720 |
| 5,233,119 | 8/1993 | Kallenbach et al. | 585/721 |

FOREIGN PATENT DOCUMENTS

0433954A1  6/1991  European Pat. Off. .

OTHER PUBLICATIONS

"Organic Chemistry" by T. W. G. Solomons, 1992, fifth edition, p. 427.
"Methyl tert-Butyl Ether and Ethyl tert-Butyl Ether" by R. Le Vanman, H. Ahlafi, and T. S. Le, ACS Symposium Series #517 (1993), pp. 233–243.
"Hydrothermal Stability of Aluminum Borate" by M. C. Tsai and Y. W. Chen, Catalysis Letters 6 (1990), p. 226.

*Primary Examiner*—Howard T. Mars
*Attorney, Agent, or Firm*—K. K. Brandes

[57] ABSTRACT

A process for simultaneously producing $C_5$–$C_{12}$ alkane(s) and $C_5$–$C_8$ tertiary alkyl ether(s) employs a liquid feed mixture containing (a) at least one $C_4$–$C_7$ isoalkane, (b) at least one second reactant which is at least one $C_4$–$C_8$ isoalkane, and/or at least one $C_4$–$C_8$ tertiary alkyl alcohol, and (c) at least one $C_1$–$C_6$ linear alkyl alcohol, wherein the liquid feed mixture is contacted at effective reaction conditions with a catalyst consisting essentially of trifluoromethanesulfonic acid and a specific solid carrier material (preferably alumina).

18 Claims, No Drawings

ALKYLATION/ETHERIFICATION PROCESS

BACKGROUND OF THE INVENTION

In one aspect, this invention relates to a process for converting isoalkanes and alcohols to a product mixture comprising higher alkanes and ethers employing a supported trifluoromethanesulfonic acid.

The use of supported trifluoromethanesulfonic acid catalysts for the alkylation of branched alkanes (isoparaffins) with alkenes (monoolefins) to higher alkanes is known and has been described in the patent literature, e.g., in U.S. Pat. No. 5,220,095. It is also known to prepare tertiary ethers (MTBE or ETBE) from branched alkenes (isoolefins) and alcohols in the presence of a catalyst comprising trifluoromethanesulfonic acid and a zeolite. The present invention is directed to a process which simultaneously converts branched alkanes and linear alcohols to a product mixture comprising both higher alkanes and tertiary ethers, in the presence of supported $CF_3SO_3H$ catalysts. This product mixture is a valuable motor fuel having a relatively low vapor pressure and a high octane rating.

SUMMARY OF THE INVENTION

It is an object of this invention to convert isoalkanes (branched alkanes) and linear alcohols to a product comprising higher branched alkanes and tertiary ethers, in the presence of a catalyst comprising trifluoromethanesulfonic acid and a solid inorganic material. Other objects and advantages will be apparent from the detailed description of the appended claims.

In accordance with this invention, a process for simultaneously producing higher branched alkanes and tertiary ethers comprises the step of contacting a liquid feed mixture comprising (a) at least one branched alkane (isoalkane) containing 4–7 carbon atoms per molecule, (b) at least one second reactant selected from the group consisting of branched alkenes (isoalkenes) containing 4–8 carbon atoms per molecule and tertiary alkyl alcohols containing one OH group and 4–8 carbon atoms per molecule, and (c) at least one linear alkyl alcohol containing one OH group and 1–6 carbon atoms per molecule with a catalyst composition consisting essentially of trifluoromethanesulfonic acid and a solid material selected from the group consisting of boria, alumina, silica, titania, zirconia, aluminum sulfate, aluminum phosphate, aluminum borate, boron phosphate, boron sulfate and mixtures of two or more than two of the above-listed materials, at effective reaction conditions so as to produce a product mixture comprising at least one branched alkane containing 5–12 carbon atoms per molecule and at least one tertiary alkyl ether containing 5–8 carbon atoms per molecule.

DETAILED DESCRIPTION OF THE INVENTION

The catalyst composition employed in the process of this invention consists essentially of $CF_3SO_3H$ on a solid inorganic carrier material. The solid inorganic material can be alumina (presently preferred), silica, silica-alumina, titania, zirconia, aluminum phosphate, aluminum oxide/phosphate, aluminum borate, aluminum borate/oxide, boron oxide, boron phosphate, aluminum/boron phosphate, boron sulfate, and mixtures thereof. Most of these solid-inorganic materials are commercially available. The preparation of others, such as aluminum phosphate on alumina and aluminum sulfate on alumina is described in U.S. Pat. No. 5,233,119. The preparation of aluminum borate/oxide is described in an article by M. C. Tsai et al in Catalysis Letters 6 (1990), page 226. Generally, the surface area of these solid inorganic materials is in the range of about 200 to about 400 $m^2/g$ (determined by the BET method of Brunauer Emmett and Teller employing $N_2$). Preferably, the particles of the solid have a size in the range of about 0.4 mm to about 0.8 mm (i.e., smaller than about 20 mesh and larger than about 40 mesh).

The catalyst compositions employed in the process of this invention can be prepared in any suitable manner. Generally, the solid inorganic material is first dried (preferably for about 0.1–20 hours at a temperature of about 100°–150° C.) and calcined (preferably for about 2–6 hours at a temperature of about 450°–600° C., more preferably about 480°–570° C., either in air or in a $N_2$ atmosphere), Thereafter, the solid inorganic material is combined with $CF_3SO_3H$, in any suitable manner. Generally, $CF_3SO_3H$ is added in liquid form to the top layer of the solid inorganic material (preferably being present in a catalyst bed) just prior to the alkylation reaction, generally at a weight ratio of $CF_3SO_3H$ to said solid inorganic material in the range of about 0.01:1 to about 0.4:1 (preferably about 0.02:1 to about 0.1:1).

In one embodiment of this invention, the liquid feed mixture comprises (a) at least one branched $C_4$–$C_7$ alkane (isoalkane, isoparaffin), (b1) at least one branched $C_4$–$C_8$ alkene (isoalkene, isoolefin) and (c) at least one linear $C_1$–$C_6$ alkyl alcohol. Non-limiting examples of suitable branched alkanes include: isobutane (presently preferred), 2-methylbutane, 2,2-dimethylpropane, 2-methylpentane, 3-methylpentane 2,2-dimethylbutane, 2,3-dimethylbutane, isoheptanes (such as methyl-substituted hexanes, dimethyl-substituted pentanes, ethyl-substituted pentanes), isooctanes (such as methyl-substituted heptanes, dimethyl-substituted hexanes, ethyl-substituted hexanes, ethyl-substituted hexanes, trimethyl-substituted pentanes, methyl, ethyl-substituted pentanes), and the like. Non-limiting examples of branched alkenes include: isobutylene (presently preferred), 2-methyl-2-butene (also presently preferred), 2-methyl-1-butene, 2-methyl-1-pentene, 2-methyl-2-pentene, 3-methyl-2-pentene, 2,2-dimethyl-1-butene, 2,2-dimethyl-2-butene, 2,3-dimethyl-1-butene, 2,3-dimethyl-2-butene, 3,3-dimethyl-1-butene, 3,3-dimethyl-2-butene, isoheptenes (such as methyl-substituted hexenes, dimethyl-substituted pentenes, ethyl-substituted pentenes, trimethyl-substituted butenes, methyl, ethyl-substituted butenes) and the like, and mixtures thereof. Non-limiting examples of linear alcohols include methanol (presently preferred), ethanol (also presently preferred), propanol, butanol-1, butanol-2 and linear pentanols, and mixtures thereof.

Any suitable content of the feed components in the liquid feed mixture can be employed. Generally, the weight percentage of component (a), i.e., isoalkane(s), in the feed is about 40–85%, preferably about 62–82%. Generally, the weight percentage of component (b2), i.e., isoalkene(s), in the feed is about 5–25%, preferably about 10–20%. And generally, the weight percentage of component (c), i.e., linear alcohol(s), in the feed is about 1–20 weight-%, preferably about 5–15 weight-%. It is within the scope of this invention to have diluents (e.g., $N_2$, linear alkanes) and/or linear alkenes (e.g., butene-2) present in the feed, generally at a level of about 0.1–30 volume-% of the liquid feed.

In another embodiment of this invention, the feed comprises (a) at least one branched $C_4$-$C_7$ alkane, (b2) at least one tertiary alkyl $C_4$-$C_8$ alcohol, and (c) at least one linear $C_1$-$C_6$ alkyl alcohol. Non-limiting examples of feed components (a) and (c) are the same as those listed above. Non-limiting examples of component (b2), i.e., tertiary alcohol(s), include t-butyl alcohol (2-methyl-2-propanol), 2-methyl-2-butanol (also called t-amyl alcohol or t-pentyl alcohol), 2-methyl-2-pentanol, 3-methyl-3-pentanol, and the like, and mixtures thereof. Any suitable content of the feed components in the feed mixture can be employed. The weight percentages of feed components (a) and (c) are the same as those listed above. Generally, the weight percentage of component (b2), i.e., tertiary alkyl alcohol(s), in the feed is about 10-35%, preferably about 20-30%. It is within the scope of this invention to have diluents (e.g., $N_2$, linear alkanes) and/or linear alkenes (e.g., butene-2) present in the feed, generally at a level of about 0.1-30 volume-% of the liquid feed.

In a further embodiment of this invention, the feed comprises components (a), (b1), (b2) and (c), as defined above. Examples of these feed components have been listed above. Generally, the weight percentages of feed components (a), (b1), (b2) and (c) are the same as those listed above. Also in this embodiment, the feed can contain diluents (e.g., $N_2$ linear alkanes) and/or linear alkenes (such as butene-2), generally at a level of about 0.1-30 volume-% of the liquid feed.

The process for simultaneously producing higher alkanes and tertiary ethers in accordance with this invention can be carried out in any suitable manner. The contacting of one of the above-described liquid feed mixtures with the supported $CF_3SO_3H$ catalyst composition (described above) can be carried out at any effective reaction conditions, generally at a relatively low temperature of up to about 70° C., preferably about $-20°$ C. to about 70° C., more preferably about 0-30° C., generally at a pressure of about 14-150 psig, preferably about 50-120 psig. Feed and formed products remain substantially in the liquid phase.

Any of the above-described liquid feed mixtures can be contacted with the catalyst composition in any suitable manner, preferably in a fixed catalyst bed operation in which the liquid feed mixture flows downward through a solid catalyst layer, generally at a liquid hourly space velocity of about 0.5-5 (preferably about 1-3) $cm^3$ feed per $cm^3$ catalyst composition per hour. The process of this invention can be carried out in a continuous manner or as a batch process. Generally, the $CF_3SO_3H$ component moves as a zone along the solid catalyst bed in the direction of the feed. When the $CF_3SO_3H$ zone approaches the exit region of the catalyst bed, the reactant flow can be reversed (so that the $CF_3SO_3H$ zone can travel back through the catalyst bed).

The process of this Invention generally generates a multitude of liquid hydrocarbon products containing a greater number of carbon atoms per molecule than the feed isoalkane(s) and also at least one liquid tertiary ether, as is demonstrated in Tables I and II. It is generally desirable to separate the formed products from unconverted feed components (hydrocarbons, alcohols). This separation can be carried out in any suitable manner, generally by fractional distillation, as can easily be determined by persons skilled in the various liquid-liquid separation technologies. It is also possible to separate the various product components from one another by known liquid-liquid separation techniques (e.g., fractional distillation). In general, however, this latter separation is not necessary because the entire product mixture can be used as a valuable motor fuel blending stock having a relatively low vapor pressure and a relatively high octane numbers.

The following examples are provided to further illustrate the processes of this invention, and are not to be construed as unduly limiting the scope of this invention.

EXAMPLE I

This example illustrates a preferred feature of the first embodiment of this invention: conversion of a feed mixture containing a branched alkane, a branched monoolefin (alkene) and a linear alcohol into a product comprising an alkylate (primarily $C_8+$ alkanes) and a tertiary ether, in the presence of a supported trifluoromethanesulfonic acid ("triflic acid") catalyst.

A U-shaped stainless steel reactor tube (inner diameter: 0.29 inch; length: 60 inches) was filled with about 40-50 grams of sized, calcined alumina ($\frac{1}{8}''$ pellets of S-100 alumina, provided by Aluminum Company of America, Pittsburgh, Pa.) which had been ground, sized to <20 to >40 mesh, and calcined in flowing $N_2$ at 500° F. for 4 hours. About 2.0 $cm^3$ of trifluoromethanesulfonic acid ("triflic acid") was then added to the top (entrance) zone of the packed column while $N_2$ gas passed through the column. The entire column was maintained at a temperature of about 64° F. A liquid alkylation feed containing various amounts of an isoalkane (isobutane), an isoalkene (isobutene or 2-methylbutene-2) and an alcohol (methanol or ethanol) was pumped through the packed column at a rate of 1 $cm^3$ per minute. The exiting alkylation/etherification product obtained at a reaction temperature of about 64° F. and a reaction pressure of about 100 psig, was analyzed about every 2 hours by means of a gas chromatograph and by simulated distillation (at atmospheric pressure). Each test lasted about 20 hours. Average test results are summarized in Table I.

TABLE I

| | Feed Composition (Weight-%) | | | (Invention) Product Composition (Weight-%) | | | | | Octane No.[2] |
|---|---|---|---|---|---|---|---|---|---|
| Run | Isoalkane | Isoalkene | Alcohol | $C_5$-$C_7$ HC[1] | $C_8$ HC[1] | $C_9$ HC[1] | $C_{10}+$ HC[1] | Ether | of Product |
| 1 | 71.5% Isobutane | 18.6% Isobutylene | 9.9% Methanol | 1.9% | 50.2% | 21.1% | 18.7% | 8.1% MTBE[4] | 93.1 |
| 2 | 71.5% Isobutane | 18.6% Isobutylene | 9.9% Methanol | 3.3% | 60.6% | 19.1% | 5.8% | 11.2% MTBE | 97.7 |
| 3[3] | 69.9% Isobutane | 10.0% Isobutylene | 10.0% Methanol | 10.6% | 24.7% | 38.0% | 11.4% | 15.3% MTBE | 93.1 |
| 4 | 81.5% Isooutane | 17.5% Isobutylene | 1.0% Methanol | 9.2% | 24.0% | 53.7% | 19.1% | 3.2% MTBE | 82.5 |
| 5 | 81.5% Isobutane | 17.5% Isobutylene | 1.0% Methanol | 5.5% | 54.2% | 32.2% | 3.1% | 5.0% MTBE | 91.4 |
| 6 | 81.5% | 17.5 | 1.0 | 3.3% | 62.3% | 25.9% | 5.7% | 2.8% | 92.4 |

TABLE I-continued

| | Feed Composition (Weight-%) | | | (Invention) Product Composition (Weight-%) | | | | | Octane No.[2] |
|---|---|---|---|---|---|---|---|---|---|
| Run | Isoalkane | Isoalkene | Alcohol | $C_5$-$C_7$ HC[1] | $C_8$ HC[1] | $C_9$ HC[1] | $C_{10}+$ HC[1] | Ether | of Product |
| 7 | Isobutane 81.5% | Isobutylene 17.5% | Methanol 1.0% | 4.4% | 61.9% | 30.1% | 1.3% | MTBE 2.3% | 91.8 |
| 8 | Isobutane 81.5% | Isobutylene 17.5% | Methanol 1.0% | 2.4% | 61.3% | 33.3% | 2.0% | MTBE 2.0% | 91.3 |
| 9 | Isobutane 81.5% | Isobutylene 17.5% | Methanol 1.0% | 1.6% | 62.4% | 25.9% | 8.4% | MTBE 1.7% | 92.1 |
| 10 | Isobutane 70.9% | Isobutylene 16.6% | Ethanol 12.5% | 11.6% | 12.5% | 40.7% | 4.5% | MTBE 30.6% ETBE[5] | 91.6 |
| 11 | Isobutane 70.9% | Isobutylene 16.6% | Ethanol 12.5% | 15.7% | 9.9% | 23.5% | 26.3% | 24.6% ETBE | 97.6 |
| 12 | Isobutane 70.8% | 2-Methyl-butene-2 16.6% | Methanol 12.0% | 11.4% | 14.7% | 38.9% | 24.5% | 10.5% TAME[6] | 88.2 |

[1] HC = hydrocarbon(s)
[2] (research octane number + motor octane number) divided by 2
[3] feed also contained 10.0 weight-% butene-2
[4] methyl tertiary-butyl ether
[5] ethyl tertiary-butyl ether
[6] tertiary-amyl methyl ether (methyl t-pentyl ether)

Test data in Table 1 clearly show that the process in accordance with this invention produces a high-octane product containing primarily $C_8+$ hydrocarbons (having a relatively low vapor pressure, being suitable as motor fuel blending stock) and a tertiary ether (MTBE, ETBE, TAME; all being valuable motor fuel oxygenated additives).

COMPARATIVE EXAMPLE IA

This example describes control runs employing 1.5 cc methanesulfonic acid on 43 g alumina (in lieu of "triflic acid" on alumina) as the catalyst. The alkylation/etherification test conditions were essentially the same as described for Example I. Test results are summarized in Table IA.

TABLE IA

| | Feed Composition (Weight-%) | | | (Control) Product Composition (Weight-%) | | | | |
|---|---|---|---|---|---|---|---|---|
| Run | Isoalkane | Isoalkene | Alcohol | $C_5$-$C_7$ HC[1] | $C_8$ HC[1] | $C_9$ HC[1] | $C_{10}+$ HC[1] | Ether |
| 13 | 70.6% Isobutane | 17.0% Isobutylene | 2.4% Ethanol | 0.0% | 0.0% | 0.0% | 0.0% | 3.2% ETBE |
| 14 | 70.8% Isobutane | 16.5% 2-Methyl-butene-2 | 12.7 Methanol | 0.0% | 0.0% | 0.0% | 0.0% | 0.0% |

[1] HC = hydrocarbons
[2] ethyl tertiary-butyl ether

Test data in Table IA clearly demonstrate that a alumina-supported methanesulfonic acid catalyst was ineffective in producing a product mixture comprising an alkylate (i.e., higher hydrocarbons) and a tertiary ether. These negative results prove that the results obtained with the alumina-supported trifluoromethane sulfonic acid ("triflic acid") catalyst in accordance with the present invention (summarized in Table I) are truly unexpected.

EXAMPLE II

This example illustrates the second embodiment of this invention: conversion of a feed mixture comprising a branched alkane, a tertiary alcohol and a linear alcohol to a product comprising an alkylate (primarily $C_8+$ hydrocarbons) and a tertiary ether in the presence of a supported trifluoromethanesulfonic acid ("triflic acid") catalyst. Test conditions were essentially the same as those described in Example I, except that different feeds were employed. Test results are summarized in Table II.

TABLE II

| | Feed Composition (Weight-%) | | | (Invention) Product Composition (Weight-%) | | | | | Octane No.[2] |
|---|---|---|---|---|---|---|---|---|---|
| Run | Isoalkane | Tertiary Alcohol | Linear Alcohol | $C_5$-$C_7$ HC[1] | $C_8$ HC[1] | $C_9$ HC[1] | $C_{10}+$ HC[1] | Ether | of Product |
| 15 | 62.4% Isobutane | 23.1% t-Butyl Alcohol | 14.5% Ethanol | 1.2% | 2.6% | 85.3% | 5.7% | 5.2% ETBE[4] | 81.9 |
| 16 | 62.4% Isobutane | 23.1% t-Butyl Alcohol | 14.5% Ethanol | 0.5% | 0.2% | 90.9% | 2.0% | 6.4% ETBE[4] | 81.5 |
| 17 | 66.9% Isobutane | 23.1% t-Butyl Alcohol | 10.0% Methanol | 3.1% | 7.0% | 73.7% | 7.0% | 9.2% MTBE[5] | 84.0 |
| 18 | 62.2% Isobutane | 27.6% t-Amyl Alcohol | 10.2% Methanol | <0.1% | 0.1% | 9.0% | 87.9% | 2.9% TAME[6] | 91.5 |
| 19[3] | 42.2% | 29.3% | 14.5% | 4.0% | 0.2% | 43.5% | 48.1% | 4.2% | 84.2 |

TABLE II-continued

| | Feed Composition (Weight-%) | | (Invention) | | | | | |
|---|---|---|---|---|---|---|---|---|
| | Tertiary | Linear | Product Composition (Weight-%) | | | | | Octane No.[2] |
| Run | Isoalkane | Alcohol | Alcohol | $C_5$-$C_7$ HC[1] | $C_8$ HC[1] | $C_9$ HC[1] | $C_{10}+$ HC[1] | Ether | of Product |
| | Isobutane | t-Amyl Alcohol | Methanol | | | | | TAME[6] | |

[1] HC = hydrocarbon(s)
[2] (research octane number + motor octane number) divided by 2
[3] feed also contains 14 weight-% butene-2
[4] ethyl tertiary-butyl ether
[5] methyl tertiary-butyl ether
[6] tertiary-amyl methyl ether Test data summarized in Table II clearly demonstrate the effectiveness of the alumina-supported "triflic acid" catalyst in the conversion of a feed comprising an isoalkane, a tertiary alcohol and a linear alcohol to an alkylate/t-ether product. The comparison of the test results of run 18 with those of run 19 shows that the additional presence of a linear olefin having an internal C=C bond (butene-2; run 19) primarily results in the production of more $C_9+$ hydrocarbons. However, the presence of a linear olefin is not necessary for producing a product comprising alkylate and tertiary ether, as is demonstrated by the results of runs 15-18.

Reasonable variations and modifications are possible within the scope of the disclosure of the invention and the appended claims.

That which is claimed is:

1. A process for simultaneously producing higher branched alkanes and tertiary ethers which comprises the step of contacting a liquid feed mixture comprising (a) at least one isoalkane containing 4-7 carbon atoms per molecule, (b) at least one second reactant selected from the group consisting of branched isoalkenes containing 4-8 carbon atoms per molecule and tertiary alkyl alcohols containing one OH group and 4-8 carbon atoms per molecule, and (c) at least one linear alkyl alcohol containing one OH group and 1-6 carbon atoms per molecule with a catalyst composition consisting essentially of trifluoromethanesulfonic acid and a solid material selected from the group consisting of boria, alumina, silica, titania, zirconia, aluminum sulfate, aluminum phosphate, aluminum borate, boron phosphate, boron sulfate and mixtures thereof, at effective reaction conditions so as to produce a product mixture comprising at least one branched alkane containing 5-12 carbon atoms per molecule and at least one tertiary alkyl ether containing 5-8 carbon atoms per molecule.

2. A process in accordance with claim 1, wherein said at least one second reactant is at least one isoalkene containing 4-8 carbon atoms per molecule.

3. A process in accordance with claim 2, wherein said liquid feed mixture comprises about 40-85 weight-% of said at least one isoalkane, about 5-25 weight-% of said at least one isoalkene, and about 1-20 weight-% of said at least one linear alkyl alcohol.

4. A process in accordance with claim 2, wherein said at least one isoalkane is isobutane, said at least one isoalkene is selected from the group consisting of isobutylene and 2-methyl-2-butene, said at least one linear alkyl alcohol is selected from the group consisting of methanol and ethanol, and said at least one tertiary alkyl ether is selected from the group consisting of methyl tertiary-butyl ether, ethyl tertiary-butyl ether and tertiary-amyl methyl ether.

5. A process in accordance with claim 4, wherein said liquid feed mixture comprises about 62-82 weight-% of said at least one isoalkane, about 10-20 weight-% of said at least one isoalkene, and about 5-15 weight-% of said at least one tertiary alkyl alcohol.

6. A process in accordance with claim 2, wherein the weight ratio of trifluoromethanesulfonic acid to said at least one solid material in said catalyst composition is in the range of about 0.01:1 to about 0.4:1.

7. A process in accordance with claim 6, wherein said solid material is alumina.

8. A process in accordance with claim 2, wherein said effective reaction conditions comprise a reaction temperature of about $-20°$ C. to about $70°$ C.

9. A process in accordance with claim 8, wherein said effective reaction conditions further comprise a pressure of about 14-150 psig and a liquid hourly space velocity of the liquid feed mixture of about 0.5-5 $cm^3$ feed per $cm^3$ catalyst composition per hour.

10. A process in accordance with claim 1, wherein said at least one second reactant is at least one tertiary alkyl alcohol containing one OH group and 4-8 carbon atoms per molecule.

11. A process in accordance with claim 10, wherein said liquid feed mixture comprises about 40-85 weight-% of said at least one isoalkane, about 10-35 weight-% of said at least one tertiary alkyl alcohol, and about 1-20 weight-% of said at least one linear alkyl alcohol.

12. A process in accordance with claim 10, wherein said at least one isoalkane is isobutane, said at least one tertiary alkyl alcohol is selected from the group consisting of tertiary-butyl alcohol and tertiary-amyl alcohol, said at least one linear alkyl alcohol is selected from the group consisting of methanol and ethanol, and said at least one tertiary alkyl ether is selected from the group consisting of methyl tertiary-butyl ether, ethyl tertiary-butyl ether and tertiary-amyl methyl ether.

13. A process in accordance with claim 12, wherein said liquid feed mixture comprises about 62-82 weight-% of said at least one isoalkane, about 20-30 weight-% of said at least one tertiary alkyl alcohol, and about 5-15 weight-% of said at least one linear alkyl alcohol.

14. A process in accordance with claim 10, wherein the weight ratio of trifluoromethanesulfonic acid to said at least one solid material in said catalyst composition is in the range of about 0.01:1 to about 0.4:1.

15. A process in accordance with claim 14, wherein said solid material is alumina.

16. A process in accordance with claim 10, wherein said effective reaction conditions comprise a reaction temperature of about $-20°$ C. to about $70°$ C.

17. A process in accordance with claim 16, wherein said effective reaction conditions further comprise a pressure of about 14-150 psig and a liquid hourly space velocity of the liquid feed mixture of about 0.5-5 $cm^3$ feed per $cm^3$ catalyst composition per hour.

18. A process in accordance with claim 1, wherein said at least one second reactant is at least one isoalkene containing 4-8 carbon atoms per molecule and additionally at least one tertiary alkyl alcohol containing 1 OH group and 4-8 carbon atoms per molecule.

* * * * *